United States Patent
Lee et al.

(10) Patent No.: US 11,380,025 B2
(45) Date of Patent: Jul. 5, 2022

(54) SCATTER CORRECTION METHOD AND APPARATUS FOR DENTAL CONE-BEAM CT

(71) Applicants: Sang Chul Lee, Yongin-si (KR); Sung Ho Chang, Osan-si (KR)

(72) Inventors: Sang Chul Lee, Yongin-si (KR); Sung Ho Chang, Osan-si (KR)

(73) Assignee: RAY CO., LTD, Hwaseong-si (KR)

( * ) Notice: Subject to any disclaimer, the term of this patent is extended or adjusted under 35 U.S.C. 154(b) by 0 days.

(21) Appl. No.: 16/757,073

(22) PCT Filed: Nov. 6, 2018

(86) PCT No.: PCT/KR2018/013344
§ 371 (c)(1),
(2) Date: Apr. 17, 2020

(87) PCT Pub. No.: WO2019/103354
PCT Pub. Date: May 31, 2019

(65) Prior Publication Data
US 2020/0279410 A1 Sep. 3, 2020

(30) Foreign Application Priority Data
Nov. 24, 2017 (KR) .................. 10-2017-0157843

(51) Int. Cl.
*G06K 9/00* (2022.01)
*G06T 11/00* (2006.01)
(Continued)

(52) U.S. Cl.
CPC .......... *G06T 11/005* (2013.01); *G06T 7/0012* (2013.01); *G06T 7/70* (2017.01);
(Continued)

(58) Field of Classification Search
CPC .................................................. G06T 11/005
See application file for complete search history.

(56) References Cited

U.S. PATENT DOCUMENTS

| 9,589,373 B2 | 3/2017 | Gindele |
| 2010/0119139 A1* | 5/2010 | Bertram ............... G06T 11/005 382/131 |

(Continued)

FOREIGN PATENT DOCUMENTS

| JP | 2009-540941 A | 11/2009 |
| KR | 10-2014-0064524 A | 5/2014 |

(Continued)

*Primary Examiner* — Oneal R Mistry
(74) *Attorney, Agent, or Firm* — John K. Park; Park Law Firm (57) ABSTRACT

The present invention relates to scatter correction method and apparatus for dental cone-beam CT. An object of the present invention is improving quality of reconstructed images by processing the scatter correction by learning which uses Monte Carlo simulation and artificial neural network. In order to achieve this object, the scatter correction method is characterized in that the method comprises steps of: rotating X-ray source of cone-beam CT in a predetermined angle while obtaining CT images for respective angles with flat-panel detector so as to reconstruct 3-dimensional CT image; generating a 2D profile of projection image by Monte Carlo simulation for respective angles by use of the reconstructed 3-dimensional CT image; decomposing the 2D profile of projection image so as to separate primary x-ray image and scatter image, wherein the primary x-ray image is unscattered in reaching the detector and wherein the scatter image is generated only by the scatter; building and doing learning of artificial neural network, wherein the objective function of the artificial neural network is primary image and scatter image which have been generated in simulation and wherein the input of the artificial neural network is the projection image which have been obtained in reality; and storing the learning information for the artificial neural network and then applying the learning information to scatter correction.

16 Claims, 4 Drawing Sheets

(51) Int. Cl.
*G06T 7/70* (2017.01)
*G06T 7/00* (2017.01)

(52) U.S. Cl.
CPC ............. *G06T 2207/10081* (2013.01); *G06T 2207/20081* (2013.01); *G06T 2207/20084* (2013.01); *G06T 2207/30008* (2013.01); *G06T 2207/30036* (2013.01); *G06T 2210/41* (2013.01)

(56) References Cited

U.S. PATENT DOCUMENTS

| | | | | |
|---|---|---|---|---|
| 2017/0265833 | A1* | 9/2017 | Danielsson | A61B 6/4291 |
| 2018/0042565 | A1* | 2/2018 | Wilson | G06T 5/009 |
| 2018/0330233 | A1* | 11/2018 | Rui | G06N 3/084 |
| 2020/0273214 | A1* | 8/2020 | Xu | G06N 3/08 |

FOREIGN PATENT DOCUMENTS

| | | |
|---|---|---|
| KR | 10-2017-0047423 A | 5/2017 |
| KR | 10-2018-0059329 A | 6/2018 |
| WO | 2003-073377 A2 | 9/2003 |

\* cited by examiner

SCATTER CORRECTION METHOD AND APPARATUS FOR DENTAL CONE-BEAM CT

FIELD OF INVENTION

The present invention relates to scatter correction method and apparatus for dental cone-beam CT (Computerized Tomography) photography which is used in taking photographs for human teeth. More specifically, the present invention relates to scatter correction method and apparatus in which scatter correction is processed by learning which uses Monte Carlo simulation and artificial neural network so as to improve the quality of reconstructed images.

BACKGROUND ART

Generally, the light has straightness and diffusivity, and the diffusivity of light causes scatter in CT photography.

Further, due to the scatter, overall images include low-frequency noise which renders the quality of reconstructed CT image lower.

Accordingly, in order to obtain high-quality image in CT photography, the scatter shall be removed from the scanning images.

The techniques for removing the scatter may include physically removing scatter or correcting scatter by estimation of scatter distribution.

Figure 1:
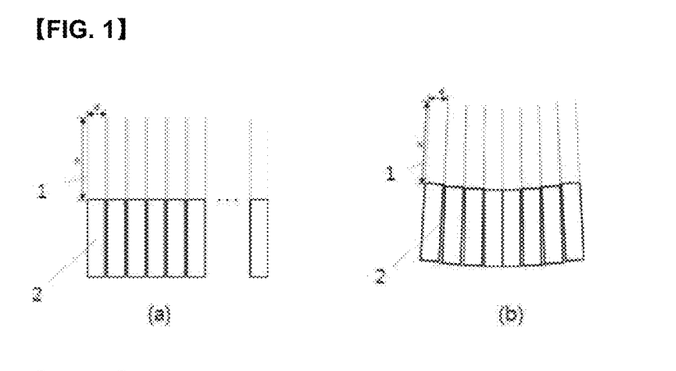
FIG. 1 is a reference view illustrating conventional approach of removing scatter by use of collimator.

As shown in FIG. 1, the technique of physically removing scatter in medical CT is based on using collimator 1 of high aspect ratio (h/d) and letting detector 2 to detect X-ray photons which coming through the collimator 1, by which the influence of the scatter may be minimized.

The collimator 1 and the detector 2 may be disposed in parallel pattern as shown in FIG. 1(a) or may be disposed in slightly-curved pattern as shown in FIG. 1(b).

Figure 2:
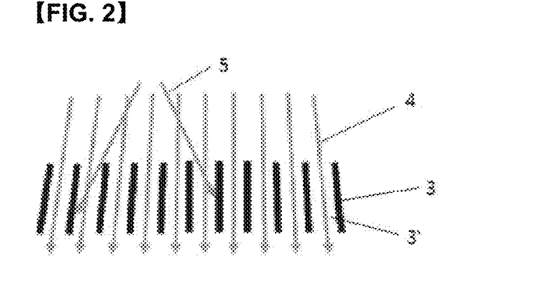
FIG. 2 is a reference view illustrating conventional approach of removing scatter by use of anti-scatter grid.

Moreover, as shown in FIG. 2, the technique of reducing X-ray scatter in digital radiography for human body is based on using anti-scatter grids 3 so as to let only the primary ray 4 to pass through the holes 3' of the anti-scatter grids 3.

That is, the influence of the scatter 5 may be minimized by letting the primary ray 4 in a line with the holes 3' of anti-scatter grids 3 pass through the holes 3' whereas letting the scatter 5 be blocked by the holes 3' of anti-scatter grids 3, Flat-panel detector is utilized in order to acquire data of daylight 4 which passes the anti-scatter grids 3.

However, with regard to the technique of physically removing scatter, the collimators as in medical CT may not be adopted in dental cone-beam CT due to structural restrictions such as pixel size and spacing.

Moreover, the usage of anti-scatter grids as in the digital radiography for human body may incur disadvantage of increase of processing time of grid lines due to increase of dose and correlation of pixel size and grid lines in images.

Alternatively, the technique of correcting scatter by estimation of scatter distribution may include measuring scatter in some area of the detector and then estimating overall scatter distribution.

However, this approach does not uses overall area of the detector but only uses some area of the detector in scatter measurement, therefore may incur disadvantage of reduction of FOV (Field of View) in CT images.

Moreover, there may be other approach of rotating X-ray source of cone-beam CT in a predetermined angle while obtaining CT images for respective angles with flat-panel detector so as to reconstruct CT image, estimating scatter distribution by Monte Carlo simulation based on the reconstructed CT image, and then re-correcting the projection image so as to reconstruct again the CT image.

However, this approach has disadvantage of long processing time of simulation which renders adaptation of real product impractical.

In the meantime, multiple patent references have been searched as prior art of the present invention, some of which are introduced below.

Patent reference 1 discloses a X-ray tomography system and a scatter correction method using the same. The X-ray tomography system includes a X-ray source of radiating X-ray toward a subject, a beam-blocking strip for blocking some of X-ray which is radiated from the X-ray source wherein the beam-blocking strip is disposed between the X-ray source and the subject and wherein a plurality of strips and spaces therebetween are alternatively disposed whose longitudinal direction is parallel placed with the rotary shaft of circular scan for the subject, a flat-panel multi-row X-ray detector of detecting X-ray penetration image data including X-ray image which may be scattered by the beam-blocking strip and the subject wherein the multi-row X-ray detector is disposed opposite to the X-ray source with respect to the subject, and image scatter correction apparatus of circularly scanning the subject, receiving the X-ray penetration image data from the multi-row X-ray detector to perform 1-dimensional scatter correction on each column of the X-ray detector which is orthogonal to the strips so as to obtain scatter image estimation data, removing the scatter image estimation data out of the X-ray penetration image data so as to obtain scatter-corrected penetration image, and performing scatter correction through the image reconstruction by use of back-projection filtering which is based on the scatter-corrected penetration image so as to obtain the reconstructed tomography image. The patent reference 1 has advantage of avoiding extra exposure of additional scanning and reducing scatter error without image distortion.

Patent reference 2 discloses a scatter removing method by use of plan CT images, which comprises steps of: obtaining image file by photographing CT image of a subject with a plan CT apparatus; transforming the image file into voxel phantom; obtaining a first cone-beam CT image by use of the voxel phantom; obtaining scatter distribution through Monte Carlo simulation of the first cone-beam CT image; obtaining a second cone-beam CT image by photographing CT image of the subject with a cone-beam CT device; and removing scatter distribution out of the second cone-beam CT image by use of the scatter distribution. The patent reference 2 provides higher accuracy because the scatter distribution does not contain inherent error which is contained conventional cone-beam CT images. Further, the patent reference 2 may quickly remove scatter distribution so as to provide the corrected images for each treatment.

DISCLOSURE OF INVENTION

Technical Problem

The present invention is proposed in order to solve the above-described problems of the convention arts. It is an object of the present invention to provide scatter correction method and apparatus for dental cone-beam CT in which scatter correction is processed by learning which uses Monte Carlo simulation and artificial neural network so as to improve the quality of reconstructed images.

Technical Solution

The scatter correction method for dental cone-beam CT according to the present invention is characterized in that the method comprises steps of: rotating X-ray source of cone-beam CT in a predetermined angle while obtaining CT images for respective angles with flat-panel detector so as to reconstruct 3-dimensional CT image; generating a 2D profile of projection image by Monte Carlo simulation for respective angles by use of the reconstructed 3-dimensional CT image; decomposing the 2D profile of projection image so as to separate primary x-ray image and scatter image, wherein the primary x-ray image is unscattered in reaching the detector and wherein the scatter image is generated only by the scatter; building and doing learning of artificial neural network, wherein the objective function of the artificial neural network is primary image and scatter image which have been generated in simulation and wherein the input of the artificial neural network is the projection image which have been obtained in reality; and storing the learning information for the artificial neural network and then applying the learning information to scatter correction.

Further, the method is characterized in that the Monte Carlo simulation is performed by use of MC simulation program of radiation particle transport which including Geant4, MCNP, Penelope and EGS.

Further, the method is characterized in that the scatter image is utilized after being performed of surface fitting by least-square or optimization.

Further, the method is characterized in that the artificial neural network is built by any one of Convolutional Neural Network (CNN), Deep Belief Network (DBN), Deep Hyper-Network (DHN), Generative Adversarial Network (GAN), and an image-based learnable artificial neural network, or combination or transformation of aforesaid.

Further, the method is characterized in that this scatter correction method is utilized for dual-energy cone-beam CT which using low-energy and high-energy.

Further, the method is characterized in that X-ray radiation conditions including tube voltage, tube current, type of filter material and filter thickness may be provided to the artificial neural network as learning data in course of doing learning of the artificial neural network.

The scatter correction apparatus for dental cone-beam CT according to the present invention is characterized by having computer program which comprising: an artificial neural network of having input of projection images for respective angles based on the CT image, of having output of scatter image or a plurality of 1D scatter profile or 2D scatter profile which are generated based on learning data, and of determining scatter profile from the projection image; and scatter-removal module of removing X-ray scatter data out of the projection image.

Further, the apparatus is characterized in that the artificial neural network may utilize as objective function of learning the scatter image which is obtained by Monte Carlo simulation on X-ray projection image for respective angles with respect to a pre-acquired CT image of subject.

Further, the apparatus is characterized in that the artificial neural network may utilize as objective function of learning the image data which is generated by performing surface fitting on the scatter image which is obtained by Monte Carlo simulation on X-ray projection image for respective angles with respect to a pre-acquired CT image of subject.

Further, the apparatus is characterized in that the artificial neural network may utilize as objective function of learning for another angle the result of interpolation of scatter image which is obtained by Monte Carlo simulation on X-ray projection image for respective angles with respect to a pre-acquired CT image of subject or the result of interpolation of the image data which is generated by performing surface fitting on the scatter image.

Further, the apparatus is characterized in that the artificial neural network may utilize as objective function of learning the primary image which is obtained by Monte Carlo simulation on X-ray projection image for respective angles with respect to a pre-acquired CT image of subject.

Further, the apparatus is characterized in that the artificial neural network may utilize as inputs of learning the projection image which is obtained in the same angle as the objective function among projection images for reconstructing the pre-acquired CT image of subject.

Further, the scatter correction apparatus for dental cone-beam CT of the present invention is characterized in that the artificial neural network may utilize as a part of inputs of learning the geometry information which including the angle in which the projection image has been obtained and distance between X-ray focus and image acquisition device.

Further, the apparatus is characterized in that the artificial neural network utilizes as a part of inputs of learning some or all of X-ray radiation conditions including tube voltage, tube current, type of filter material and filter thickness.

Further, the apparatus is characterized by having computer program including an artificial neural network of having input of projection images for respective angles based on the CT image, of having output of X-ray image with scatter removed wherein the X-ray image is generated based on learning data, and of determining scatter profile from the projection image so as to output image which be removed from scatter.

Advantageous Effects

The present invention may provide an advantage of minimizing the effect of scatter and improving the image quality of reconstructed image by performing Monte Carlo simulation so as to decompose each of projection images which are obtained for respective angles in a cone-beam CT or a dual-energy cone-beam CT and further by do learning scatter information with artificial neural network so as to utilize the learning information in scatter correction.

Further, the present invention may provide other advantage of improving image quality of reconstructed image and correction quality with use by reinforcing scatter matters by iterative learning of artificial neural network.

Further, the present invention may provide other advantage of gradually improving image quality of reconstructed image by utilizing various image data for objective function in learning of artificial neural network and by removing scatter by use of learning data which has been stored in the learning of artificial neural network.

BEST EMBODIMENT FOR CARRYING OUT THE INVENTION

There shall be described in detail as below the preferred embodiment of the scatter correction method and apparatus for dental cone-beam CT according to the present invention with referring to the accompanying drawings.

Figure 3:
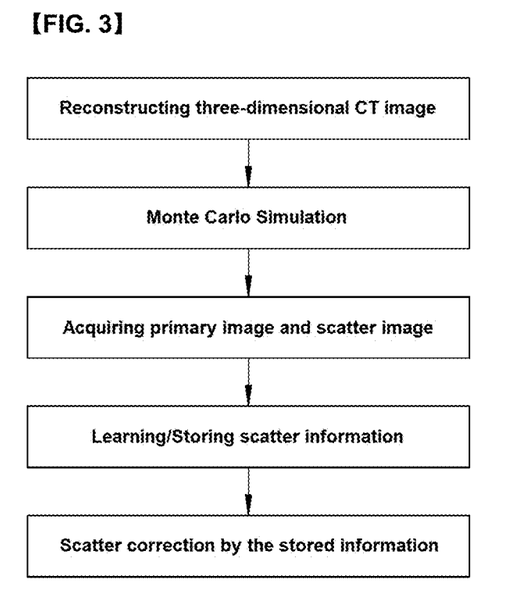
FIG. 3 is a flowchart illustrating scatter correction method for dental cone-beam CT according to the present invention.

As shown in FIG. 3, the scatter correction method for dental cone-beam CT according to the present invention comprises steps of rotating X-ray source of cone-beam CT in a predetermined angle while obtaining CT images for respective angles with flat-panel detector so as to reconstruct 3-dimensional CT image; generating a 2D profile of projection image by Monte Carlo simulation for respective angles by use of the reconstructed 3-dimensional CT image; decomposing the 2D profile of projection image so as to separate primary x-ray image and scatter image, wherein the primary x-ray image is unscattered in reaching the detector and wherein the scatter image is generated only by the scatter; building and doing learning of artificial neural network, wherein the objective function of the artificial neural network is primary image and scatter image which have been generated in simulation and wherein the input of the artificial neural network is the projection image which have been obtained in reality; and storing the learning information for the artificial neural network and then applying the learning information to scatter correction.

Further, Monte Carlo simulation is performed by use of MC simulation program of radiation particle transport which including Geant4, MCNP, Penelope and EGS.

Further, scatter image may be used as it is, or may be utilized after being performed of surface fitting by least-square or optimization.

Further, artificial neural network is built by any one of Convolutional Neural Network (CNN), Deep Belief Network (DBN), Deep HyperNetwork (DHN), Generative Adversarial Network (GAN), and an image-based learnable artificial neural network, or combination or transformation of aforesaid.

Further, X-ray radiation conditions including tube voltage, tube current, type of filter material and filter thickness may be provided to the artificial neural network as learning data in course of doing learning of the artificial neural network.

The scatter correction method for dental cone-beam CT according to the present invention may be utilized for general cone-beam CT which using a single energy, or may be utilized for dual-energy cone-beam CT which using low-energy and high-energy.

In the dual-energy cone-beam CT, teeth image information may be obtained by radiating X-ray of different energy levels.

Figure 4:
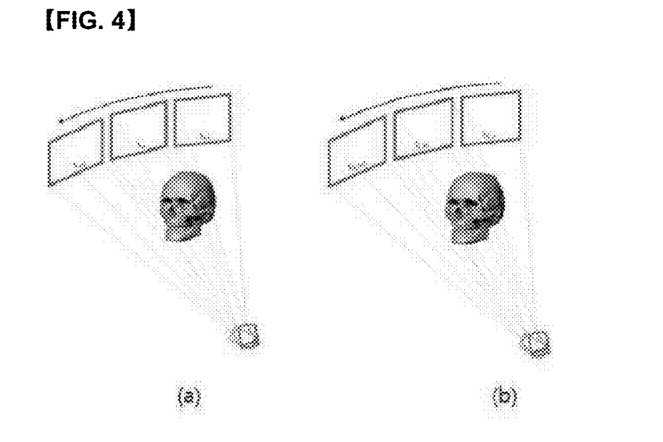
FIG. 4 is an exemplary view illustrating Monte Carlo simulation for respective angles of CT acquisition.

As shown in FIG. 4, the scatter correction method for dental cone-beam CT according to the present invention generates image or profile of the unscattered primary X-ray and the scattered X-ray in reaching the detector by Monte Carlo simulation for respective angles by use of reconstructed 3-dimensional CT image of previous patients.

Figure 5:
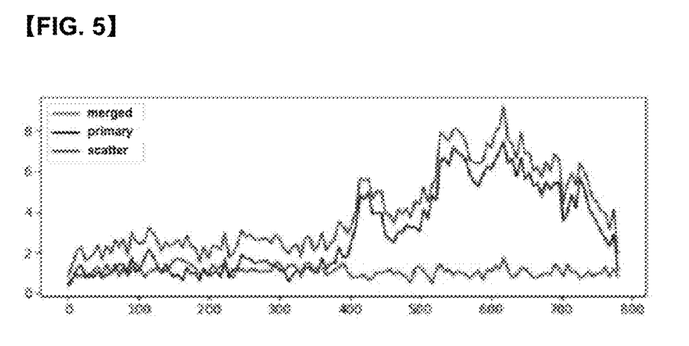
FIG. 5 is an exemplary view illustrating primary and scatter profile on a line for the same projection image.

Accordingly, as shown in FIG. 5, the profiles for the same location of each image may be obtained.

Figure 6:
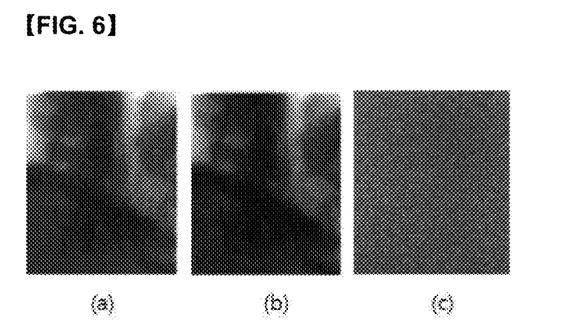
FIG. 6 is an exemplary view showing images of Monte Carlo simulation.

Further, the projection image as shown in FIG. 6(a) which is obtained by simulation may be decomposed into the primary image as shown in FIG. 6(b) in which X-ray is unaffected in reaching the detector and the scatter image as shown in FIG. 6(c) in which only scatter is involved in image generation.

Figure 7:
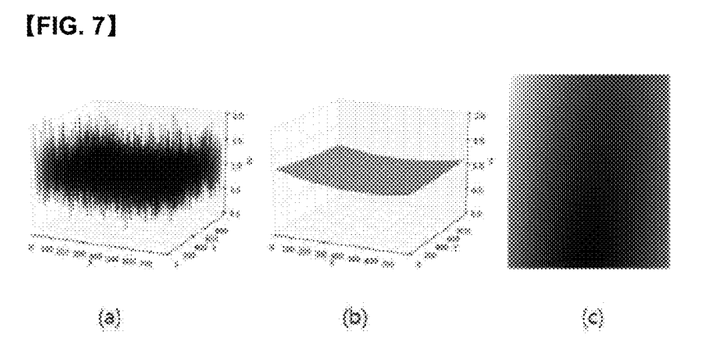
FIG. 7 is an exemplary view illustrating surface fitting on scatter images of FIG. 6.

Further, because the scatter image generally contains statistical noise, as shown in FIG. 7, it is preferable that the scatter image is utilized after being performed of surface fitting by least-square or optimization.

For reference, FIG. 7(a) shows a surface plot of scatter image. FIG. 7(b) shows a surface plot of scatter image after surface fitting. FIG. 7(c) shows scatter image after surface fitting.

Figure 8:
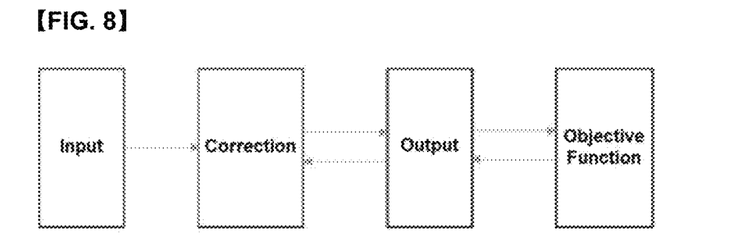
FIG. 8 is a schematic view of artificial neural network which learns according to the present invention.

Further, as shown in FIG. 8, the scatter correction apparatus for dental cone-beam CT according to the present invention is characterized by having computer program which comprising: an artificial neural network of having input of projection images for respective angles based on the CT image, of having output of scatter image or a plurality of 1D scatter profile or 2D scatter profile which are generated based on learning data, and of determining scatter profile from the projection image; and scatter-removal module of removing X-ray scatter data out of the projection image.

The computer program does learning artificial neural network with utilizing as an input the projection image which has been acquired from a patient in reality and with utilizing as objective function or objective data the primary or 2D profile of scatters which has been obtained by Monte Carlo simulation on CT image data for the same patient. Then, the computer program generates 2D profile of scatters based on the learning data for each of projection image which is acquired in CT photography of patients in reality, and then removing the 2D profile of scatters out of the projection image. Alternatively, the computer program generates primary image based on the learning data for each of projection image which is acquired in CT photography of patients in reality.

The artificial neural network may utilize as objective function of learning the scatter image which is obtained by Monte Carlo simulation on X-ray projection image for respective angles with respect to a pre-acquired CT image of subject. Further, the artificial neural network may utilize as objective function of learning the image data which is generated by performing surface fitting on the scatter image which is obtained by Monte Carlo simulation on X-ray projection image for respective angles with respect to a pre-acquired CT image of subject.

Further, the artificial neural network may utilize as objective function of learning for another angle the result of interpolation of scatter image which is obtained by Monte Carlo simulation on X-ray projection image for respective angles with respect to a pre-acquired CT image of subject or the result of interpolation of the image data which is generated by performing surface fitting on the scatter image. Further, the artificial neural network may utilize as objective function of learning the primary image which is obtained by Monte Carlo simulation on X-ray projection image for respective angles with respect to a pre-acquired CT image of subject.

Further, the artificial neural network may utilize as inputs of learning the projection image which is obtained in the same angle as the objective function among projection images for reconstructing the pre-acquired CT image of subject.

Further, the artificial neural network may utilize as a part of inputs of learning the geometry information which including the angle in which the projection image has been obtained and distance between X-ray focus and image acquisition device.

Further, the artificial neural network may utilize as a part of inputs of learning some or all of X-ray radiation conditions including tube voltage, tube current, type of filter material and filter thickness.

Figure 9:
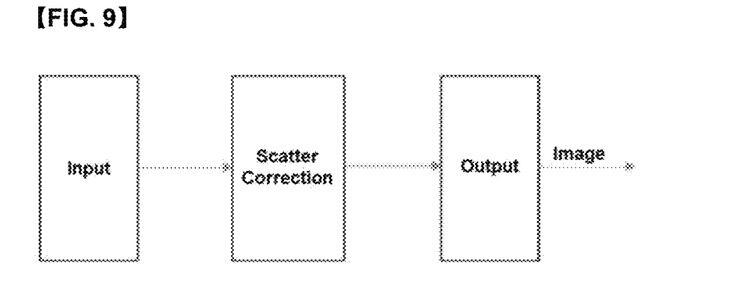
FIG. 9 is a schematic view of artificial neural network which corrects scatters according to the present invention.

Further, as shown in FIG. 9, the scatter correction apparatus for dental cone-beam CT according to the present invention is characterized by having computer program including an artificial neural network of having input of projection images for respective angles based on the CT image, of having output of X-ray image with scatter removed wherein the X-ray image is generated based on learning data, and of determining scatter profile from the projection image so as to output image which be removed from scatter.

The preferred embodiment of the present invention has been described above only for examplary purpose. Therefore, the present invention shall not be limited thereto. Those of ordinary skill in the art will appreciate that various modifications and other equivalent embodiments thereof are available without departing from the technical spirit of the present invention.

The invention claimed is:

1. A scatter correction method for dental cone-beam CT, the method comprising:
rotating X-ray source of cone-beam CT in a predetermined angle while obtaining CT images for respective angles with flat-panel detector so as to reconstruct 3-dimensional CT image;
generating a 2D profile of projection image by Monte Carlo simulation for respective angles by use of the reconstructed 3-dimensional CT image;
decomposing the 2D profile of projection image so as to separate primary x-ray image and scatter image, wherein the primary x-ray image is unscattered in reaching the detector and wherein the scatter image is generated only by the scatter;
performing surface fitting on the scatter image by least-square or optimization so as to remove statistical noise out of the scatter image;
building and doing learning of artificial neural network, wherein the objective function of the artificial neural network is primary image and scatter image which have been generated in simulation and wherein the input of the artificial neural network is the projection image which have been obtained in reality;
storing the learning information for the artificial neural network; and
applying the learning information to scatter correction.

2. The method according to claim 1, wherein the Monte Carlo simulation is performed by use of MC simulation program of radiation particle transport which including Geant4, MCNP, Penelope and EGS.

3. The method according to claim 1, wherein the artificial neural network is built by any one of Convolutional Neural Network (CNN), Deep Belief Network (DBN), Deep Hyper-Network (DHN), Generative Adversarial Network (GAN), and an image-based learnable artificial neural network, or combination or transformation of aforesaid.

4. The method according to claim 1, wherein X-ray radiation conditions including tube voltage, tube current, type of filter material and filter thickness may be provided to the artificial neural network as learning data in course of doing learning of the artificial neural network.

5. Scatter correction apparatus for dental cone-beam CT, the apparatus having computer program which comprising: an artificial neural network of having input of projection images for respective angles based on the CT image, of having output of scatter image or a plurality of 1D scatter profile or 2D scatter profile which are generated based on learning data, and of determining scatter profile from the projection image; and scatter-removal module of removing X-ray scatter data out of the projection image, wherein the artificial neural network utilizes, as objective function of learning, the scatter image which is obtained by Monte Carlo simulation on X-ray projection image for respective angles with respect to a pre-acquired CT image of subject, and wherein surface fitting is performed on the scatter image by least-square or optimization so as to remove statistical noise out of the scatter image for utilized as the objective function of learning.

6. The apparatus according to claim 5, wherein the artificial neural network utilizes, as objective function of learning for another angle, the result of interpolation of scatter image which is obtained by Monte Carlo simulation on X-ray projection image for respective angles with respect to a pre-acquired CT image of subject or the result of interpolation of the image data which is generated by performing surface fitting on the scatter image.

7. The apparatus according to claim 5, wherein the artificial neural network further utilizes, as objective function of learning, the primary image which is obtained by Monte Carlo simulation on X-ray projection image for respective angles with respect to a pre-acquired CT image of subject.

8. The apparatus according to claim 5, wherein the artificial neural network utilizes, as inputs of learning, the projection image which is obtained in the same angle as the objective function among projection images for reconstructing the pre-acquired CT image of subject.

9. The apparatus according to claim 5, wherein the artificial neural network utilizes, as a part of inputs of learning, the geometry information which including the angle in which the projection image has been obtained and distance between X-ray focus and image acquisition device.

10. The apparatus according to claim 5, wherein the artificial neural network utilizes, as a part of inputs of learning, some or all of X-ray radiation conditions including tube voltage, tube current, type of filter material and filter thickness.

11. Scatter correction apparatus for dental cone-beam CT, the apparatus having computer program including an artificial neural network of having input of projection images for respective angles based on the CT image, of having output of X-ray image with scatter removed wherein the X-ray image is generated based on learning data, and of determining scatter profile from the projection image so as to output image which be removed from scatter, wherein the artificial neural network utilizes, as objective function of learning, the scatter image which is obtained by Monte Carlo simulation on X-ray projection image for respective angles with respect to a pre-acquired CT image of subject, and wherein surface fitting is performed on the scatter image by least-square or optimization so as to remove statistical noise out of the scatter image for utilized as the objective function of learning.

12. The apparatus according to claim 11, wherein the artificial neural network utilizes, as objective function of learning for another angle, the result of interpolation of scatter image which is obtained by Monte Carlo simulation on X-ray projection image for respective angles with respect to a pre-acquired CT image of subject or the result of interpolation of the image data which is generated by performing surface fitting on the scatter image.

13. The apparatus according to claim 11, wherein the artificial neural network further utilizes, as objective function of learning, the primary image which is obtained by Monte Carlo simulation on X-ray projection image for respective angles with respect to a pre-acquired CT image of subject.

14. The apparatus according to claim 11, wherein the artificial neural network utilizes, as inputs of learning, the projection image which is obtained in the same angle as the objective function among projection images for reconstructing the pre-acquired CT image of subject.

15. The apparatus according to claim 11, wherein the artificial neural network utilizes, as a part of inputs of learning, the geometry information which including the angle in which the projection image has been obtained and distance between X-ray focus and image acquisition device.

16. The apparatus according to claim 11, wherein the artificial neural network utilizes, as a part of inputs of learning, some or all of X-ray radiation conditions including tube voltage, tube current, type of filter material and filter thickness.

* * * * *